(12) United States Patent
Park et al.

(10) Patent No.: US 11,800,858 B2
(45) Date of Patent: Oct. 31, 2023

(54) MOUSE WITH CHOLINERGIC NEURON-SPECIFIC INACTIVATED ANO1 GENE

(71) Applicant: Korea University Research and Business Foundation, Seoul (KR)

(72) Inventors: Jae-Yong Park, Seoul (KR); Eun Mi Hwang, Seoul (KR); Heh-In Im, Seongnam-si (KR); Chang-Hoon Cho, Seoul (KR); Sangjoon Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 217 days.

(21) Appl. No.: 16/643,184

(22) PCT Filed: Jul. 20, 2018

(86) PCT No.: PCT/KR2018/008217
§ 371 (c)(1),
(2) Date: Feb. 28, 2020

(87) PCT Pub. No.: WO2019/045273
PCT Pub. Date: Mar. 7, 2019

(65) Prior Publication Data
US 2020/0187467 A1    Jun. 18, 2020

(30) Foreign Application Priority Data

Aug. 31, 2017  (KR) .................. 10-2017-0110930
Jul. 19, 2018  (KR) .................. 10-2018-0084365

(51) Int. Cl.
| | |
|---|---|
| *A01K 67/027* | (2006.01) |
| *A61K 49/00* | (2006.01) |
| *C07K 14/47* | (2006.01) |
| *C07K 14/705* | (2006.01) |
| *G01N 33/68* | (2006.01) |
| *G01N 33/50* | (2006.01) |

(52) U.S. Cl.
CPC ...... *A01K 67/0276* (2013.01); *A61K 49/0008* (2013.01); *C07K 14/47* (2013.01); *C07K 14/705* (2013.01); *G01N 33/5088* (2013.01); *G01N 33/6896* (2013.01); *A01K 2217/054* (2013.01); *A01K 2217/075* (2013.01); *A01K 2217/206* (2013.01); *A01K 2227/105* (2013.01); *A01K 2267/0318* (2013.01); *A01K 2267/0356* (2013.01); *G01N 2800/302* (2013.01)

(58) Field of Classification Search
None
See application file for complete search history.

(56) References Cited

FOREIGN PATENT DOCUMENTS

| KR | 10-1127756 B1 | 3/2012 |
| KR | 10-2015-0001435 A | 1/2015 |
| KR | 10-2017-0022715 A | 3/2017 |

OTHER PUBLICATIONS

MGI description of "enhanced behavioral reswponse to cocain", 2022.*
Powell (Biol Psychiatry, 2006, vol. 59, p. 1198-1207).*
Giacopuzzi (Plos, 2017, vol. 12, No. 8, e0182778).*
Satou (Frontiers in Physiology, 2017, vol. 8, Article 320, p. 1-8).*
Boskovic (J. Neurosci., 2014, vol. 34, No. 39, p. 13033-13038).*
Ryouichi Satou et al., "Temporal Expression Patterns of Clock Genes and Aquaporin 5/Anoctamin 1 in Rat Submandibular Gland Cells", Frontiers in Physiology, May 23, 2017, pp. 1-8, vol. 8, Article 320.
Asma Amjad et al., "Conditional knockout of TMEM16A/anoctamin1 abolishes the calcium-activated chloride current in mouse vomeronasal sensory neurons", The Journal of General Physiology, Mar. 16, 2015, pp. 285-301, vol. 145, No. 4.
International Search Report for PCT/KR2018/008217, dated Oct. 26, 2018.
Byeongjun Lee et al., "Anoctamin 1 contributes to inflammatory and nerve-injury induced hypersensitivity", Molecular Pain, 2014, vol. 10, No. 5, pp. 285-301 (9 pages total).

\* cited by examiner

*Primary Examiner* — Michael C Wilson
(74) *Attorney, Agent, or Firm* — Sughrue Mion, PLLC (57) ABSTRACT

The present invention relates to: A schizophrenia animal model wherein the model is a mouse in which an anoctamin 1 (ANO1) gene is knocked out in cholinergic neurons of a medial habenula; and a preparation method therefor and the like. The schizophrenia animal model according to the present invention targets the medial habenula which is brain tissue playing a major role in the pathogenesis of schizophrenia, and it has been confirmed that when the ANO1 gene is specifically knocked out in the cholinergic neurons of the medial habenula, positive, negative and cognitive symptoms of schizophrenia are observed, thereby confirming that schizophrenia has been induced. Therefore, the animal model of the present invention is expected to be effectively useful in schizophrenia pathogenesis research and therapeutic agent development and screening.

4 Claims, 10 Drawing Sheets

MOUSE WITH CHOLINERGIC NEURON-SPECIFIC INACTIVATED ANO1 GENE

CROSS REFERENCE TO RELATED APPLICATIONS

This application is a 371 of PCT/KR2018/008217, filed Jul. 20, 2018, which claims the benefit of priority from Korean Patent Application No. 10-2017-0110930, filed Aug. 31, 2017, and Korean Patent Application No. 10-2018-0084365, filed Jul. 19, 2018, the contents of each of which are incorporated herein by reference in its entirety.

TECHNICAL FIELD

The present invention relates to a schizophrenia animal model, wherein the model is a mouse in which an anoctamin 1 (ANO1; TMEM16A) gene is specifically knocked out in cholinergic neurons of medial habenula, and a method of preparing the same.

BACKGROUND ART

Schizophrenia is a severe mental illness characterized by inappropriate understanding of oneself or the outside world, confusion of thought, behavioral disorders with a lack of reality, and 1% of the world's population suffers from this disease. Schizophrenic symptoms may be divided into three subgroups, which are most generally positive symptoms (hallucinations, delusions, etc.), negative symptoms (anhedonia, asociality, etc.) and cognitive symptoms (cognitive deficits, emotional disturbance, etc.), according to the causes of symptoms and diagnostic criteria. Diagnosis of schizophrenia is made when most specific symptoms persist for over 1 month, or some symptoms persist over 6 months.

Schizophrenia requires specific drug treatment, separate from psychological therapies, and conventional and typical antipsychotic medications have focused on treatment of positive symptoms such as hallucinations, delusions and confusion. It is known that a dopamine D2 receptor antagonist has been known to be effective in treating schizophrenia, and particularly, haloperidol, chlorpromazine, fluphenazine and the like are used. However, research on the molecular-biological pathogenesis of schizophrenia is relatively insufficient.

Brain tissues known to play a major role in the onset of schizophrenia are largely limited to the prefrontal cortex and striatum. As human genome research continues, genetic factors associated with the onset of schizophrenia have been reported, which however suggests only their statistical correlation with the incidence of schizophrenia, but the effect of the reported function of an allele on the actual onset of schizophrenia is little known. In addition, while research of the effect of environmental factors on the onset of schizophrenia is also progressing, it is difficult to obtain accurate results from population studies including actual patient groups due to realistic limits such as costs, the limit of research subjects, etc. Therefore, to compensate for clinical research, attempts to develop various schizophrenia animal models continue, but there is still a lack of adequate animal models to be utilized in the study of molecular/genetic mechanisms of schizophrenia and validation of a therapeutic agent for schizophrenia.

Transgenic animals refer to animals in which a desired genetic trait is expressed by artificially inserting a foreign gene or eliminating a gene, and can be useful for basic research to identify the role of specific genes in living organisms. That is, by inserting or deleting a gene to be studied and observing the effect manifested by the gene, the physiological function mediated by the gene may be inferred. In addition, transgenic animals can be used as a model for a human disease, and very effectively used to identify the cause or progression of a disease, or confirm an effect or shortcoming of a potential medication. Currently, transgenic mice, zebrafish and the like, which have diseases such as dementia, cancer, heart diseases and genetic diseases, are being developed (Korean Patent No. KR 10-1750893), and among them, as schizophrenia animal models, disrupted in schizophrenia 1 (DISC1), Neuregulin1 (NRG1), Dystrobrevin-binding protein 1 (DTNBP1) and reelin mutant gene-introduced mouse models are known.

Meanwhile, anoctamin 1 (ANO1; TMEM16A) gene is located on chromosome band 11q13, and overexpressed in various types of cancer cells such as head and neck cancer, breast cancer and prostate cancer. As the role of ANO1 protein as a chlorine ion channel activated by calcium was identified in 2008, functional studies using electrophysiological techniques have been actively conducted. In the case of cancer cells with increased ANO1 expression, it has been recently found that the growth of the cancer cells was inhibited by suppression of the expression of the ANO1 gene itself, and therefore, the ANO1 gene is attracting attention as a target of novel anticancer therapy. However, nothing has been known about the correlation between schizophrenia and the ANO1 gene.

As a result of intensive efforts for the development of a novel schizophrenia animal model, the inventors confirmed that a mouse in which the ANO1 gene is specifically knocked out in cholinergic neurons of the medial habenula shows schizophrenic symptoms, and based on this, a transgenic animal that is able to be used as a schizophrenia animal model can be effectively prepared. Finally, the present invention was completed.

DISCLOSURE

Technical Problem

As the inventors had studied brain tissue involved in the onset of schizophrenia, and confirmed that a mouse in which ANO1 gene is specifically knocked out in cholinergic neurons of the medial habenula exhibits schizophrenic symptoms, and therefore, the present invention was completed.

Therefore, the present invention is directed to providing a schizophrenia animal model and a method of preparing the same.

The present invention is also directed to providing a method of screening a schizophrenia therapeutic agent.

However, technical problems to be solved in the present invention are not limited to the above-described problems, and other problems which are not described herein will be fully understood by those of ordinary skill in the art from the following descriptions.

Technical Solution

To attain the above-mentioned objects of the present invention, one aspect of the present invention provides a schizophrenia animal model wherein the model is a mouse in which an anoctamin 1 (ANO1) gene is knocked out in cholinergic neurons of medial habenula.

In one embodiment of the present invention, the mouse may be a homozygote or a heterozygote.

Another aspect of the present invention provides a method of preparing a schizophrenia animal model, which comprises: obtaining second generation mice by crossing a choline acetyltransferase (ChAT)-Cre mouse and an ANO1 floxed mouse; and selecting a mouse in which the ANO1 gene is not expressed in cholinergic neurons of medial habenula from the second generation mice.

In one embodiment of the present invention, the ChAT-Cre mouse may be a mouse in which Cre recombinase is expressed under the control of a promoter of ChAT.

In another embodiment of the present invention, the ANO1 floxed mouse may be a mouse in which loxP base sequences are inserted at both sides of exon8 of ANO1.

In still another embodiment of the present invention, the selection of a mouse in which the ANO1 gene is not expressed in cholinergic neurons of the medial habenula may be performed by polymerase chain reaction (PCR) and immunohistochemistry.

Still another aspect of the present invention provides a method of screening a schizophrenia therapeutic agent, which comprises: treating the schizophrenia animal model with a test material; measuring schizophrenic symptoms after the treatment of the test material; and selecting a test material which significantly decreases schizophrenic symptoms, as compared with an untreated group.

In one embodiment of the present invention, the test material may be a candidate for a schizophrenia therapeutic agent.

In another embodiment of the present invention, the measurement of the schizophrenic symptoms may be performed using a 3-chamber test (3CT), a nestlet shredding test, a passive avoidance test, a cocaine sensitization test, or a prepulse inhibition test.

Advantageous Effects

The schizophrenic animal model according to the present invention is a novel genetic model that targets the medial habenula, which is the brain tissue that mainly acts on the schizophrenia pathogenesis, unlike the previously known DISC1, NRG1, DTNBP1, and Reelin mutant transgenic schizophrenic animal models. The mouse in which ANO1 gene is specifically knocked out in cholinergic neurons of the medial habenula showed positive, negative, and cognitive symptoms of schizophrenia, and is expected to be an ideal animal model to replace the majority of schizophrenic patients with complex and diverse symptoms. In addition, the animal model of the present invention can be usefully used to identify the association between the genetic/environmental factors and behavioral abnormalities of schizophrenia, and to screen and verify schizophrenia therapeutic drugs.

DESCRIPTION OF DRAWINGS

FIGS. 2A to 2C show the results of a 3-chamber test (3CT) for a mouse prepared according to the present invention (cKO) and a normal mouse (CTL), in which

MODES OF THE INVENTION

The inventors prepared a mouse in which ANO1 gene is specifically knocked out in cholinergic neurons of the medial habenula using a Cre/Lox genetic system (refer to FIG. 1A and Example 1), and confirmed that the prepared mouse exhibits all of negative, positive and cognitive symptoms of schizophrenia, thereby confirming that the animal model of the present invention can be used as an animal model effective for drug validation for the research of molecular/genetic mechanisms of schizophrenia and schizophrenia treatment. Therefore, the present invention provides a schizophrenia animal model in which the ANO1 gene is specifically knocked out in cholinergic neurons of medial habenula, a method of preparing the same, and a method of screening a schizophrenia therapeutic agent using the same.

The "medial habenula" used herein is a brain region receiving nerve signals from various brain regions (ex. limbic system). It receives nerve signals from basal ganglia and cerebral limbic system and sends nerve signals to forebrain and midbrain structures containing dopamine and serotonin neurons. The medial habenula is involved in pain progression, reproductive activity, nutrition, a sleep-wake cycle, stress response, and learning.

The "cholinergic neuron" used herein refers to a nerve cell secreting acetylcholine as a neurotransmitter. The cholinergic neurons are known to be directly involved in the onset of a brain-nervous system disease of an animal, and it is also known that damage to cholinergic neurons is accompanied with the onset of various degenerative brain diseases such as Alzheimer's disease, Parkinson's disease, amyotrophic lateral sclerosis, etc.

The "anoctamin 1 (ANO1)" used herein is known as a gene encoding transmembrane member 16A (TMEM16A), and is a gene of a chloride ion channel. The chloride ion channel is involved in mucous secretion from cells after chloride anions are released from smooth muscle and epithelial cells, and the human body performs biological activities such as the secretion of saliva, tears and sweat, and fluid absorption in the kidneys and stomach through the above-mentioned process.

The "ANO1 gene is specifically knocked out in cholinergic neurons of the medial habenula" used herein means the conditional knock-out (cKO) of ANO1 gene only in cholinergic neurons of medial habenula, while the ANO1 gene is expressed in other tissue.

The term "knock-out" used herein means partial, substantial, complete knock-out or inactivation of a gene.

The present invention also provides a method of preparing a schizophrenia animal model, which comprises: obtaining second generation mice by crossing a ChAT-Cre mouse and an ANO1 floxed mouse; and selecting a mouse in which ANO1 gene is not expressed in cholinergic neurons of the medial habenula from the second generation mice.

The "Cre/Lox genetic system" used herein is a powerful system for controlling the expression of two genes (Cre and Lox) derived from P1 bacteriophages, and particularly, a research tool which is well established in a mouse transformation field. Cre recombinase catalyzes site-specific recombination between two loxP sites that can be located on the same or separate DNA fragments. Two 13bp repeat sequences at a single loxP site are recognized by and bound with the Cre protein, thereby forming a dimer, and two loxP sites are arranged in a parallel orientation and form a tetramer with four Cre proteins. Double-stranded DNA may be cleaved in a core spacer at each loxP site, and the two strands are connected and crossed to delete DNA, such that transgenic animals having desired DNA may be obtained.

Meanwhile, the schizophrenia animal model of the present invention is not limited as long as it is any animal capable of being raised in a cage, except a human, and may include a rodent, a rabbit and a monkey, and preferably, a laboratory mouse or rat.

A mouse belonging to rodents is most commonly used in an animal test, and particularly, the laboratory mouse is *Mus musculus* (mouse) and *Rattus norvegicus* (rat), respectively, which are advantageous as a laboratory animal due to easy raising, fast breeding and a low cost, and is more appropriate as a schizophrenia animal model because research on behavioral patterns corresponding to various symptoms of schizophrenia patients has matured. In the present invention, the laboratory mouse is used in the sense to include a mouse and a rat, and the laboratory mouse and rat used herein are referred to as mouse.

In the present invention, measurement of the schizophrenic symptoms may be performed using a 3-chamber test (3CT), a prepulse inhibition test, a nesting behavior test, a barbering behavior test or a social dominance test, and preferably, a 3CT, a nestlet shredding test, a passive avoidance test, a cocaine sensitization test, or a prepulse inhibition test, but the present invention is not limited thereto.

Figure 1A:
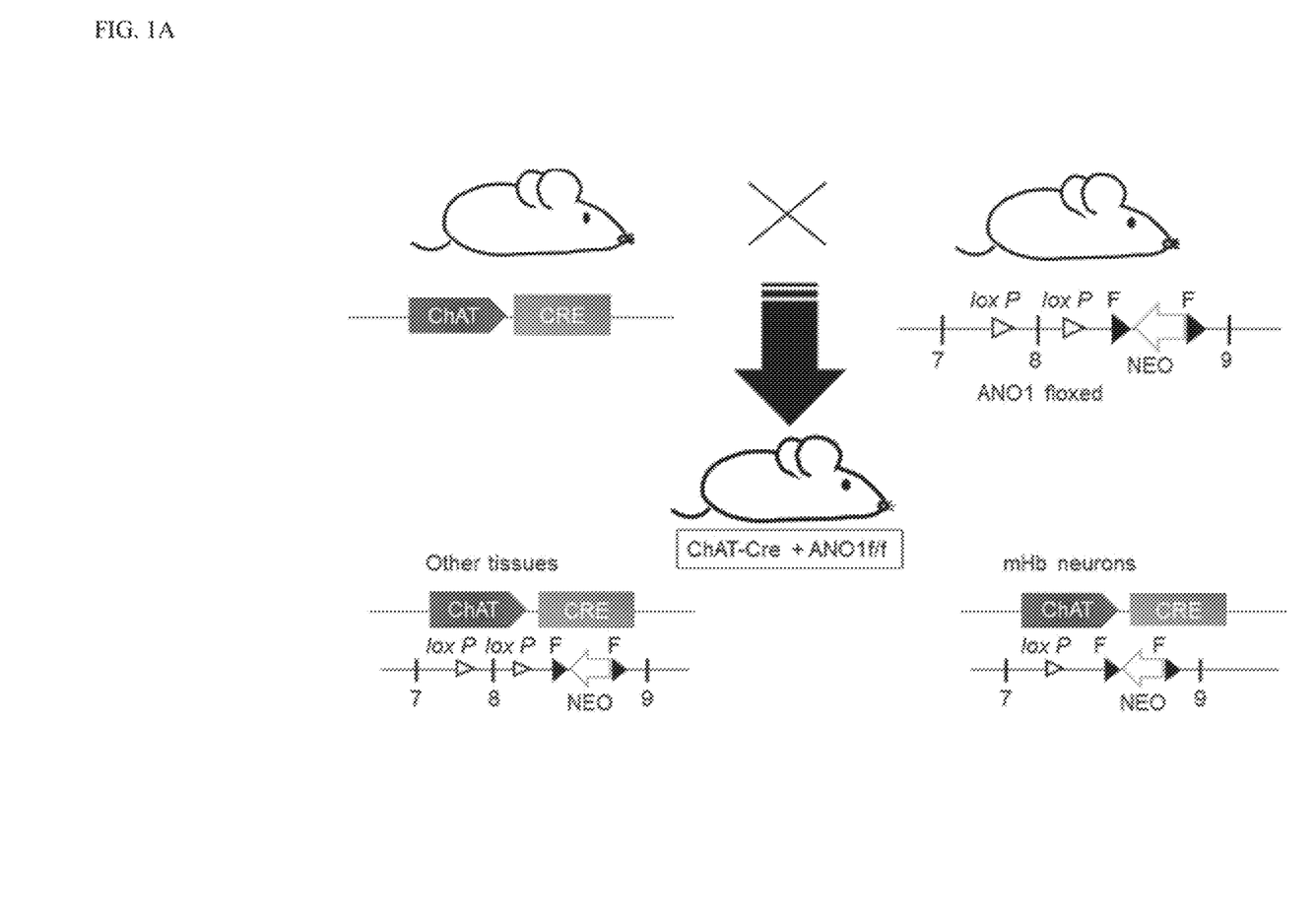
FIG. 1A is a schematic diagram illustrating a method of preparing a mouse in which ANO1 gene is knocked out in cholinergic neurons of the medial habenula.

In one embodiment of the present invention, to prepare a transgenic mouse in which the expression of the ANO1 chloride ion channel gene is specifically knocked out in cholinergic neurons of the medial habenula, exon8 of the ANO1 gene is eliminated in cholinergic neurons by Cre recombinase by crossing Cre recombinase-expressing ChAT-Cre mice under the control of a promoter in choline acetyltransferase (ChAT), which is a cholinergic neuron-specific gene, and ANO1 floxed mice in which loxP base sequences are inserted at both sides of exon8 of ANO1 such that mice in which the expression of the ANO1 ion channel is selectively eliminated in cholinergic neurons of the medial habenula are prepared (refer to FIG. 1A and Example 1). In another embodiment of the present invention, to confirm whether the prepared mouse (cKO) is a mouse in which the ANO1 gene is specifically knocked out in cholinergic neurons of the medial habenula, immunohistochemistry is performed using an antibody against the ANO1 ion channel protein and an antibody against ChAT protein and 4',6-diamidino-2-phenylindole (DAPI) for labeling a cell nucleus so as to confirm that the absence of the ANO1 protein expression in cholinergic neurons of the medial habenula of a mouse (cKO) in which the ANO1 gene is specifically knocked out in cholinergic neurons of the medial habenula is completely eliminated (refer to FIG. 1B and Example 1).

Meanwhile, the "schizophrenia" to be studied using an animal model of the present invention is a mental illness showing a combination of various symptoms, and since schizophrenia is accompanied by not only characteristic symptoms distinguished from other mental illnesses, but also symptoms that can be diagnosed in other various mental illnesses such as depression, comprehensive judgment is important in schizophrenia diagnosis.

As described above, the schizophrenic symptoms may be classified into positive, negative and cognitive symptoms according to the causes of symptoms and diagnostic criteria. Each type of symptoms may be distinguished corresponding to representative behavioral patterns shown in schizophrenia animal models.

Meanwhile, the negative symptom of schizophrenia refers to a phenomenon in which emotional and active functions weaken or disappear, which may be confirmed by a social interaction test for an animal model.

One of the negative symptoms of schizophrenia is a lack of social motivation (including social isolation and social atrophy), which is shown in schizophrenia patients, and to measure it in the schizophrenia animal model, a behavioral test method for measuring intimacy between individuals is applied. A mouse, a social animal, basically expresses curiosity and intimacy when encountering other mice of the same kind, but it can be confirmed that, in the schizophrenia animal model, the lack of social expression can be observed in certain experimental settings. For example, reduction in the place preference for a place with isolated mice of the same kind indicates the lack of sociality. In addition, since an urge to prepare a home in rodents (nesting behavior) is also known to as an instinct reflecting cooperation and sociality, it is able to be used as a critical indicator of sociality. While a normal mouse makes a nest shape using a nesting material, a schizophrenia model mouse relatively lacks such a behavioral characteristic.

Therefore, in one embodiment of the present invention, to confirm whether the animal model of the present invention shows a negative symptom of schizophrenia, a 3CT test and a nestlet shredding test were performed. As a result, it can be confirmed that the mouse (cKO) in which the ANO1 gene is specifically knocked out in cholinergic neurons of the medial habenula, compared with the normal mouse (CTL), showed a very low interest in mice of the same kind, and the nesting behavior is reduced (refer to Examples 2 and 3). From this, it can be seen that the animal model of the present invention can be provided as a suitable animal model for investigating a negative symptom of schizophrenia.

In addition, the cognitive symptoms of schizophrenia include attention deficit, abnormal sensorimotor synchronization, etc. A phenomenon in which the learning content about a particular stimulus is difficult to be replaced with another result is referred to as potential suppression, and it has been noted that schizophrenia patients are abnormal in such potential suppressing capacity. In the animal model, potential suppression was measured through a fear conditioning paradigm.

Therefore, in one embodiment of the present invention, the inventors carried out a passive avoidance test to confirm whether the animal model of the present invention shows a cognitive symptom of schizophrenia. As a result, the mouse (cKO) in which the ANO1 gene is specifically knocked out in cholinergic neurons of the medial habenula according to the present invention, compared with the normal mouse (CTL), has a short time for re-entering the stimulus due to the decrease in learning and memory of a negative stimulus (refer to Example 4). From this result, it can be seen that the animal model of the present invention can be provided as a suitable animal model for investigating schizophrenia cognitive symptoms. In addition, the positive symptoms of schizophrenia are symptoms which are difficult to be realized and confirmed in an animal model, for example, delusions, hallucinations, threatening speech, auditory hallucinations, etc., but some behavioral patterns may be indirectly identified from a prepulse inhibition (PPI) test and a sensitization test for a psychoactive drug (e.g., cocaine) in a schizophrenia animal model.

Generally, a normal person shows insensitive responses to repeated and identical stimuli, compared with a degree of the first response to a strong sensory stimulus, while schizophrenia patients are known to show sensitive responses to repeated sensory stimuli. A phenomenon of reducing PPI shown in the schizophrenia patient may be measured and confirmed by almost the same method even in the schizophrenia animal model. In addition, cocaine that stimulates the dopamine system has been known to induce psychosis in a normal person or worsen symptoms of the schizophrenia patient. The mouse animal model also shows similar hyperactivity to the schizophrenia patient in response to cocaine, considered as one behavior associated with the positive symptoms.

Therefore, in one embodiment of the present invention, the inventors carried out a prepulse inhibition test to confirm whether the animal model of the present invention shows a positive symptom of schizophrenia. As a result, it can be confirmed that responses to repeated stimuli are maintained and thus prepulse inhibition is reduced. It was also confirmed that prepulse inhibition is restored to a normal mouse level by administering haloperidol used in the clinic as an agent for relieving schizophrenic symptoms to the animal model of the present invention (refer to Example 5). In addition, the inventors carried out a cocaine sensitization test to confirm the positive symptoms of schizophrenia shown in the animal model of the present invention in various aspects. As a result, the mouse (cKO) in which the ANO1 gene is specifically knocked out in cholinergic neurons of the medial habenula according to the present invention, compared with the normal mouse (CTL), shows significantly greater movement. Therefore, it can be confirmed that the animal model of the present invention sensitively responds to a psychoactive drug and thus can be provided as a suitable animal model for investigating positive symptoms of schizophrenia (refer to Example 6).

From this result, it can be seen that the animal model of the present invention can be provided as a suitable animal model for investigating schizophrenia positive symptoms.

That is, the mouse in which the ANO1 gene is specifically knocked out in cholinergic neurons of the medial habenula according to the present invention is an ideal animal model that can represent most schizophrenia patient groups having complicated and various symptoms due to expressing all of positive, negative and cognitive symptoms shown in schizophrenia, and thus can be used as a useful animal model for investigating schizophrenia.

In addition, the animal model of the present invention can be effectively used to identify the correlation between genetic/environmental causes and behavior abnormalities, screen a therapeutic agent for schizophrenia, and validate the agent.

EXAMPLES

As the present invention may have various modifications and embodiments, specific embodiments will be described in further detail below. However, the present invention is not limited to the specific embodiments, and it should be understood that the present invention includes all modifications, equivalents and alternatives included in the technical idea and scope of the present invention. In describing the present invention, if it is determined that a detailed description of the related art may obscure the gist of the present invention, the detailed description thereof will be omitted.

Hereinafter, to help in understanding the present invention, exemplary examples will be suggested. However, the following examples are merely provided to more easily understand the present invention, and not to limit the present invention.

Example 1. Preparation of Mouse in which Anoctamin 1 (ANO1) Gene is Specifically Knocked Out in Cholinergic Neurons of Medial Habenula Using Cre/Lox Genetic System To prepare a transgenic mouse in which the expression of ANO1 chloride ion channel gene was specifically knocked out in cholinergic neurons of the medial habenula, a ChAT-Cre mouse in which Cre recombinase was expressed under the control of a promoter of choline acetyltransferase (ChAT), which is a cholinergic neuron-specific expression gene, was crossed with ANO1 floxed mouse in which a loxP base sequence was inserted at both sides of exon8 of ANO1 (Cho et al., 2012 Nature Neuroscience 15, 1015; prepared by Prof. Uhtaek Oh, KIST). A mouse in which the expression of the ANO1 ion channel is selectively eliminated in cholinergic neurons of the medial habenula was prepared by eliminating exon8 of the ANO1 gene by Cre recombinase in cholinergic neurons in the mouse prepared by crossbreeding (refer to FIG. 1A).

To confirm whether the prepared mouse (cKO) is a mouse in which the ANO1 gene was specifically knocked out in cholinergic neurons of the medial habenula, immunohistochemistry was performed using an antibody against ANO1 ion channel protein (Abcam), an antibody against ChAT protein (Merck Millipore) and 4',6-diamidino-2-phenylindole (DAPI; Sigma-Aldrich, USA) for labeling a cell nucleus. As a control, a normal mouse (CTL) was used. A signal of the cell nuclear marker DAPI was indicated in blue (refer to the left panel of FIG. 1B), in green when the ANO1 ion channel protein was expressed (refer to the central panel of FIG. 1B), in yellow when the both the ANO1 ion channel protein and the ChAT protein were expressed, and in red when only the ChAT protein was expressed (refer to the right panel of FIG. 1B).

Figure 1B:
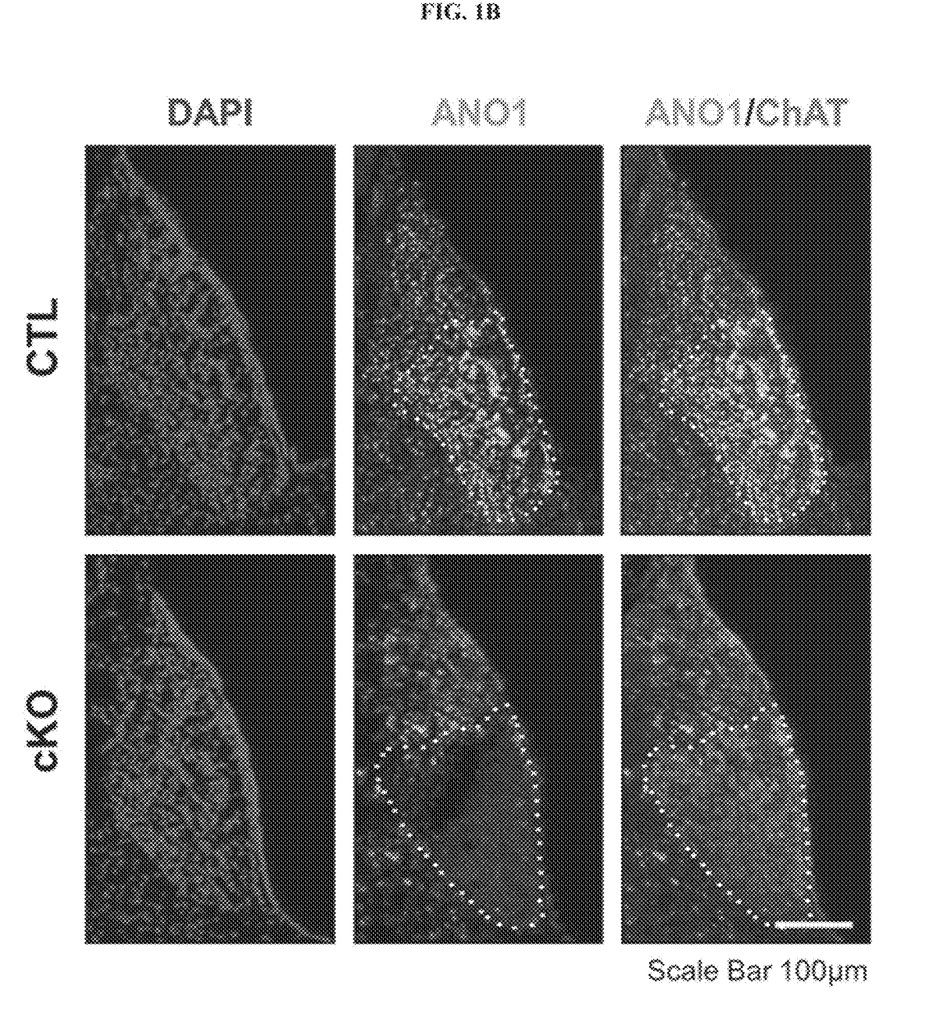
FIG. 1B shows the results obtained by immunohistochemistry to confirm whether a mouse prepared according to the present invention (cKO) is a mouse in which ANO1 gene is specifically knocked out in cholinergic neurons of the medial habenula.

As a result, as shown in FIG. 1B, it was confirmed that the ChAT protein is expressed in both of the normal mouse (CTL) and the mouse (cKO) in which the ANO1 gene was specifically knocked out in cholinergic neurons of the medial habenula, but it was confirmed that the expression of the ANO1 ion channel protein is completely eliminated in cholinergic neurons of the medial habenula in the mouse (cKO) in which the ANO1 gene was specifically knocked out in cholinergic neurons of the medial habenula.

Example 2. 3-Chamber Test (3CT)

To confirm whether the mouse in which the ANO1 gene was specifically knocked out in cholinergic neurons of the medial habenula, which was prepared by the method described in Example 1, shows negative symptoms of schizophrenia, 3CT, which is the most widely used behavior test for confirming the sociality of mice, was performed. Specifically, measurement mice (8- to 14-week-old, males) were put into the middle of three sequential chambers, which are separated by a transparent wall, in EthoVision XT 11.5 (Noldus, Netherlands). One mouse (S1) was put in one of the side chambers, an inanimate object (O) (refer to FIG. 2B), or a living mouse (S1) shown in FIG. 2B and a new mouse (S2) (refer to FIG. 2C) were put in the opposite side chamber, and then a long-staying position was indicated in red. The test was carried out for 10 minutes, and as a control, a normal mouse (CTL), which is a littermate of the test animal, was used.

Figure 2A:
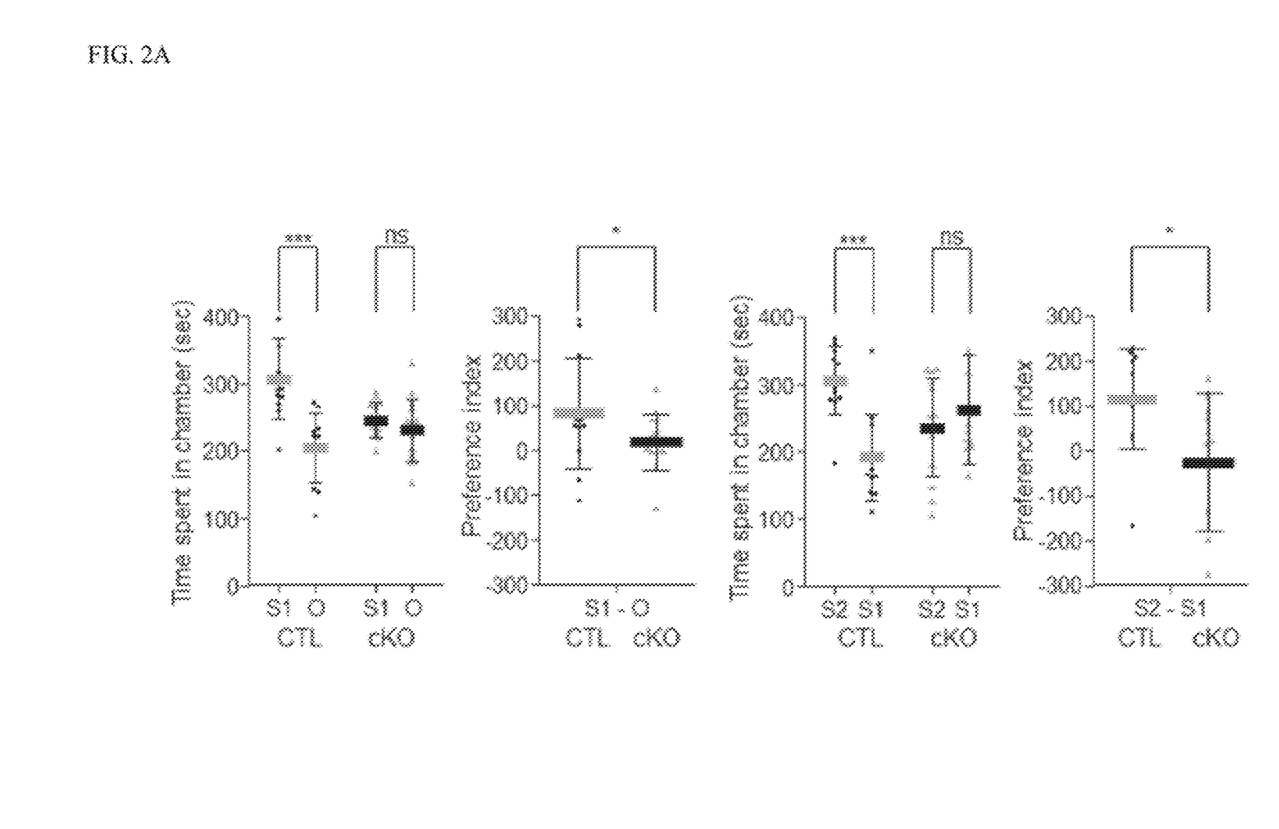
FIG. 2A is a set of graphs of the staying time in each chamber and preferences for the chambers of the mouse prepared according to the present invention (cKO) and the normal mouse (CTL)
Figure 2B:
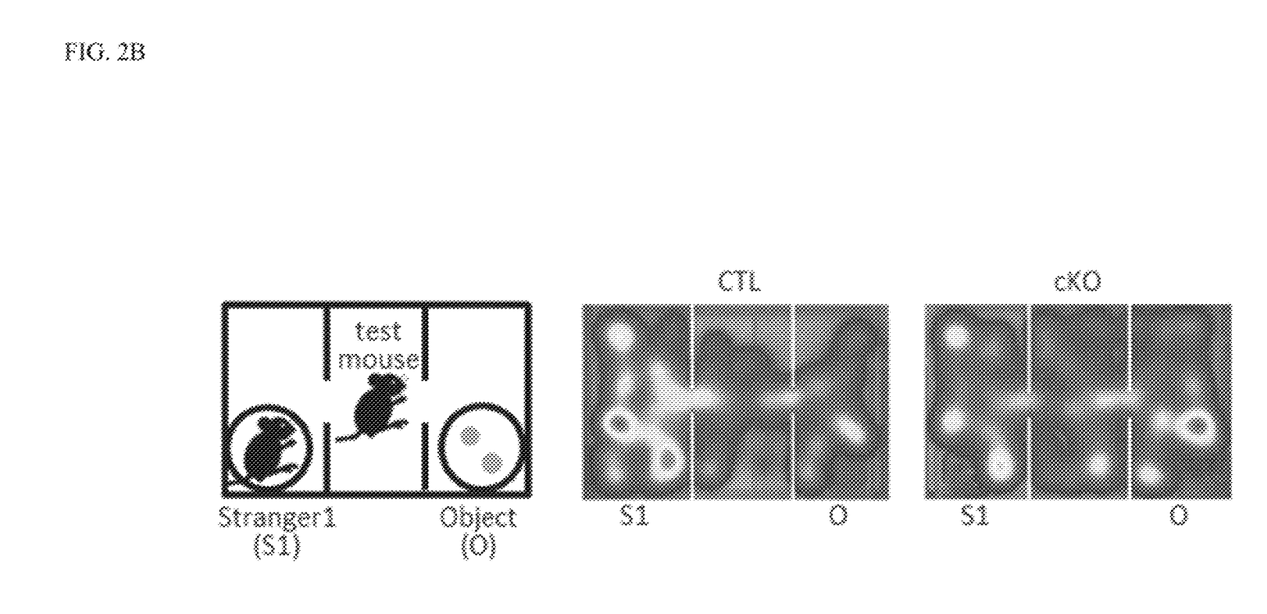
FIG. 2B shows the degrees of interest of the mouse prepared according to the present invention (cKO) and the normal mouse (CTL) on an inanimate object (O) and a living mouse (S1)

As a result, as shown in the two left panels of FIG. 2A and FIG. 2B, it was confirmed that the normal mouse (CTL) shows a meaningful interest in the living mouse (S1), rather than the inanimate object (O), but the mouse (cKO) in which the ANO1 gene was specifically knocked out in cholinergic neurons of the medial habenula shows similar degrees of interest in the object (O) and the living mouse (S1).

Figure 2C:
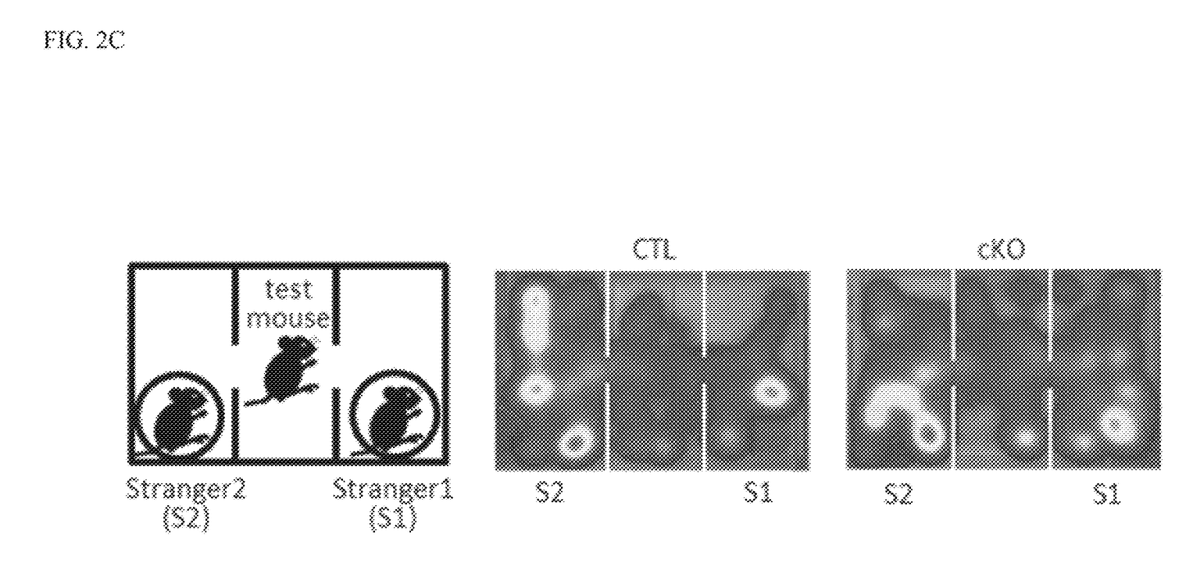
FIG. 2C shows the degrees of interest of the mouse prepared according to the present invention (cKO) and the normal mouse (CTL) on the living mouse (S1) shown in FIG. 2B and a new mouse (S2).

In addition, as shown in the two right panels of FIG. 2A and FIG. 2C, it was confirmed that the normal mouse (CTL) shows more interest in the new mouse (S2), than the living mouse (S1) shown in FIG. 2B, but the mouse (cKO) in which the ANO1 gene was specifically knocked out in cholinergic neurons of the medial habenula shows similar degrees of interest in the object (O) and the living mouse (S1).

From the above result, it can be seen that the mouse (cKO) in which the ANO1 gene was specifically knocked out in cholinergic neurons of the medial habenula was reduced in curiosity and intimacy with respect to a mouse of the same kind, and lacked social sensibility.

Example 3. Nestlet Shredding Test

Following the test of confirming a lack of sociality described in Example 2, a nestlet shredding test was performed to confirm whether the mouse in which the ANO1 gene was specifically knocked out in cholinergic neurons of the medial habenula, which was prepared by the method of Example 1, shows the negative symptoms of schizophrenia in more various aspects. Particularly, a previously weighed nestlet (5×5 cm) and a measurement mouse were put in a transparent plastic mouse cage (19×29×13 cm). After one hour, the weight of an unshredded nestlet was measured, and then the weight of a nestlet shredded by the ANO1 gene-knocked out mouse (cKO) and the weight of a nestlet shredded by the normal mouse were compared.

Figure 3:
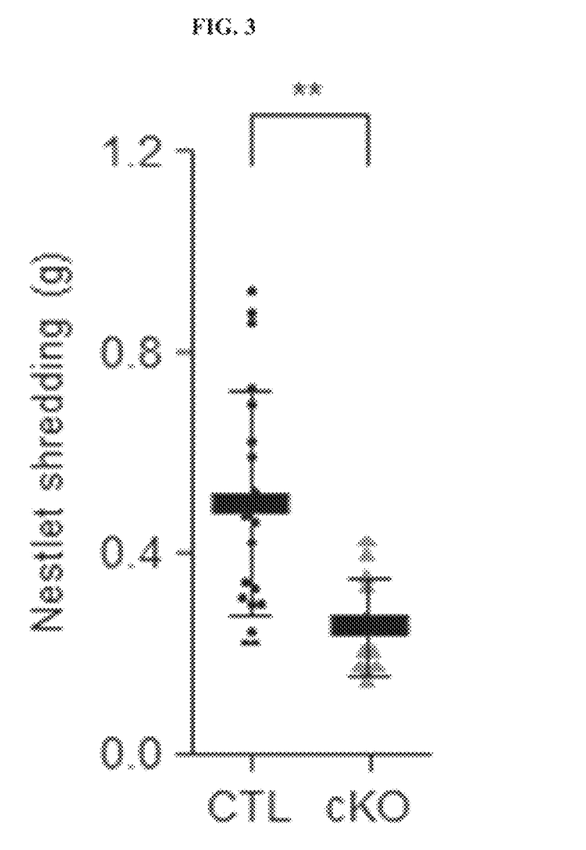
FIG. 3 shows the result of a nestlet shredding test for a mouse prepared according to the present invention (cKO) and a normal mouse (CTL).

As a result, as shown in FIG. 3, it can be confirmed that the mouse (cKO) in which the ANO1 gene was specifically knocked out in cholinergic neurons of the medial habenula shredded less neslet than the normal mouse (CTL), and it can be seen that the normal mouse shredded nestlets approximately twice as much as the ANO1 gene-knocked out mouse (cKO) to form a nest. From the result, it can be confirmed that the nature of the ANO1 gene-knocked out mouse (cKO) for reflecting cooperation and sociality was reduced, compared with the normal mouse.

Example 4. Passive Avoidance Test

A passive avoidance test, which is most commonly used among behavioral tests for confirming learning and memory capacities of a mouse, was performed to confirm whether the mouse in which the ANO1 gene was specifically knocked out in cholinergic neurons of the medial habenula, which was prepared by the method described in Example 1, shows the cognitive symptoms of schizophrenia. Particularly, measurement mice were acclimated in a quiet and dark experimental space for 20 minutes, and then each mouse was placed in a bright part in the experimental space of two chambers. After one minute, a door to the other dark chamber was open to let the mouse enter the chamber. When the whole body of the mouse entered the dark chamber, the door was closed and then an electrical shock (0.45 mV, 2 sec) was applied to the bottom of the chamber. The following day, the same experiment was repeated, but an electrical shock was not applied when the mouse entered the dark chamber. Here, the time for entering the dark place was measured and then compared with time of the previous day, such that the avoidance behavior by the learning and memory of the mouse was observed.

Figure 4:
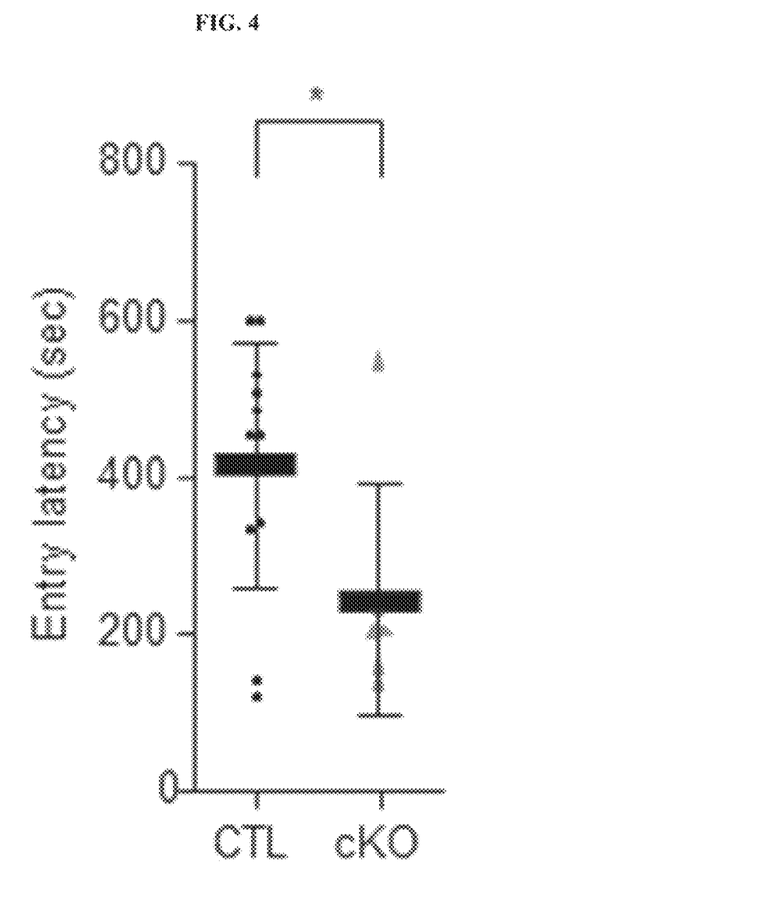
FIG. 4 shows the result of a passive avoidance test for a mouse prepared according to the present invention (cKO) and a normal mouse (CTL).

As a result, as shown in FIG. 4, the mouse (cKO) in which the ANO1 gene was specifically knocked out in cholinergic neurons of the medial habenula took a shorter time to reenter a dark place, compared with the normal mouse (CTL), specifically, the ANO1 gene-knocked out mouse (cKO) entered the dark place about twice as fast as the normal mouse. From the result, it can be confirmed that the ANO1 gene-knocked out mouse (cKO) shows a lack of memory and learning of a negative stimulus, compared with the normal mouse.

Example 5. Prepulse Inhibition Test (PPI Test)

To confirm whether the mouse in which the ANO1 gene was specifically knocked out in cholinergic neurons of the medial habenula, which was prepared by the method described in Example 1, shows positive symptoms of schizophrenia, a PPI test for measuring a degree of surprise about an auditory stimulus was performed. Particularly, the test was performed on a group of 8 mice (8- to 14-week old, male) in one acoustic startle chamber (Coulbourn instrument). The startle reflex was triggered by a pulse stimulus in the form of the burst of 65 dB white noise (SS). The inhibition of SS-induced startle responses was performed using a 120-mB, 40-msec prepulse stimulus with various intensities (74, 82 and 90-dB white noise) preceding 100-msec SS.

The test was designed with the array of seven blocks, each block was separated into the "semi-random" combination of eight different test types (trial type, non-stimulus, SS only, three types of PP only, three types of PP and SS) at intervals of 10 to 15 seconds. Percent prepulse inhibition (% PPI) was calculated by [1−(response to PP-SS coupling/response to SS only)]×100.

Figure 5:
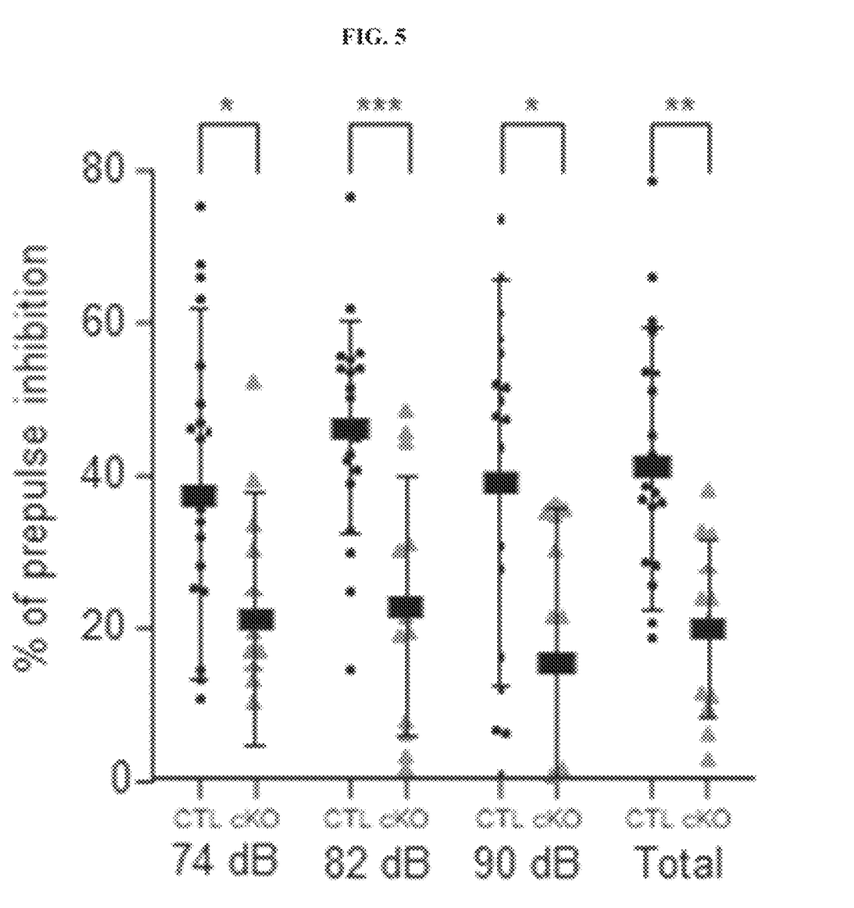
FIG. 5 shows the result of a prepulse inhibition test (PPI test) for a mouse prepared according to the present invention (cKO) and a normal mouse (CTL).

As a result, as shown in FIG. 5, it was confirmed that a phenomenon (PPI) of less sensitively responding to a stronger stimulus after the preceding weak stimulus was significantly inhibited in the mouse (cKO) in which the ANO1 gene was specifically knocked out in cholinergic neurons of the medial habenula. It is demonstrated that the mouse (cKO) in which the ANO1 gene was specifically knocked out in cholinergic neurons of the medial habenula shows schizophrenic symptoms.

Figure 6:
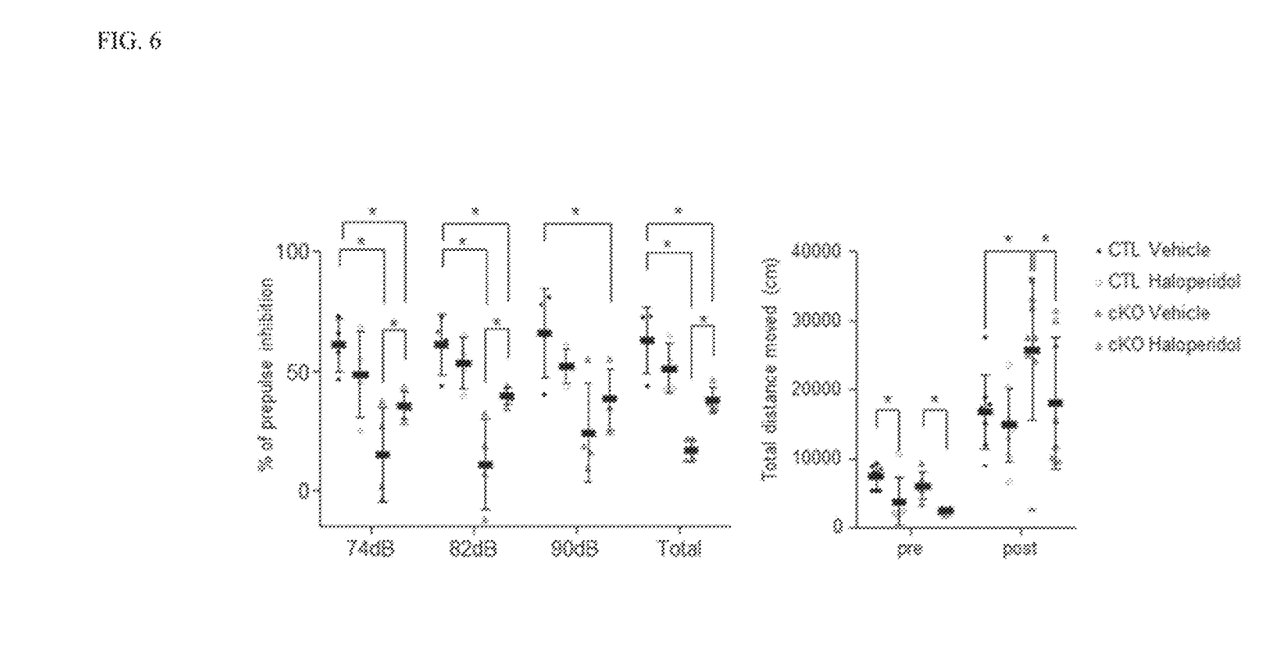
FIG. 6 shows haloperidol effects on a mouse prepared according to the present invention (cKO) and a normal mouse (CTL) in a prepulse inhibition test (PPI test).

It was also demonstrated that schizophrenic symptoms were improved in the PPI test for the mouse (cKO) in which the ANO1 gene was specifically knocked out in cholinergic neurons of the medial habenula by intraperitoneally administering haloperidol (0.1 mg/kg of body weight, Tocris, USA), which is clinically used as a symptom relieving agent for schizophrenia patients, 30 minutes before the test (refer to FIG. 6). As a vehicle, 0.3 M HCl (pH 5.5-6.0) was used. A haloperidol stock solution was prepared in 0.3 M HCl (pH 5.5-6.0), and stored for up to a month at 20° C.

This shows that the ANO1 cKO mouse can be used as an excellent schizophrenia mouse model.

Example 6. Cocaine Sensitization Test

To confirm whether the mouse in which the ANO1 gene was specifically knocked out in cholinergic neurons of the medial habenula, which was prepared by the method described in Example 1, shows positive symptoms of schizophrenia, a sensitization test for a psychoactive drug, cocaine, was performed. Particularly, measurement mice (8 to 14-week old, male) were administered cocaine (15 mg/kg) by intraperitoneal injection, a total distance of movement for 30 minutes before/after cocaine administration in an open space (40×40 cm) was measured to observe an activity pattern. As a control, normal mouse (CTL), which is a littermate administered saline by intraperitoneal injection, was used.

Figure 7:
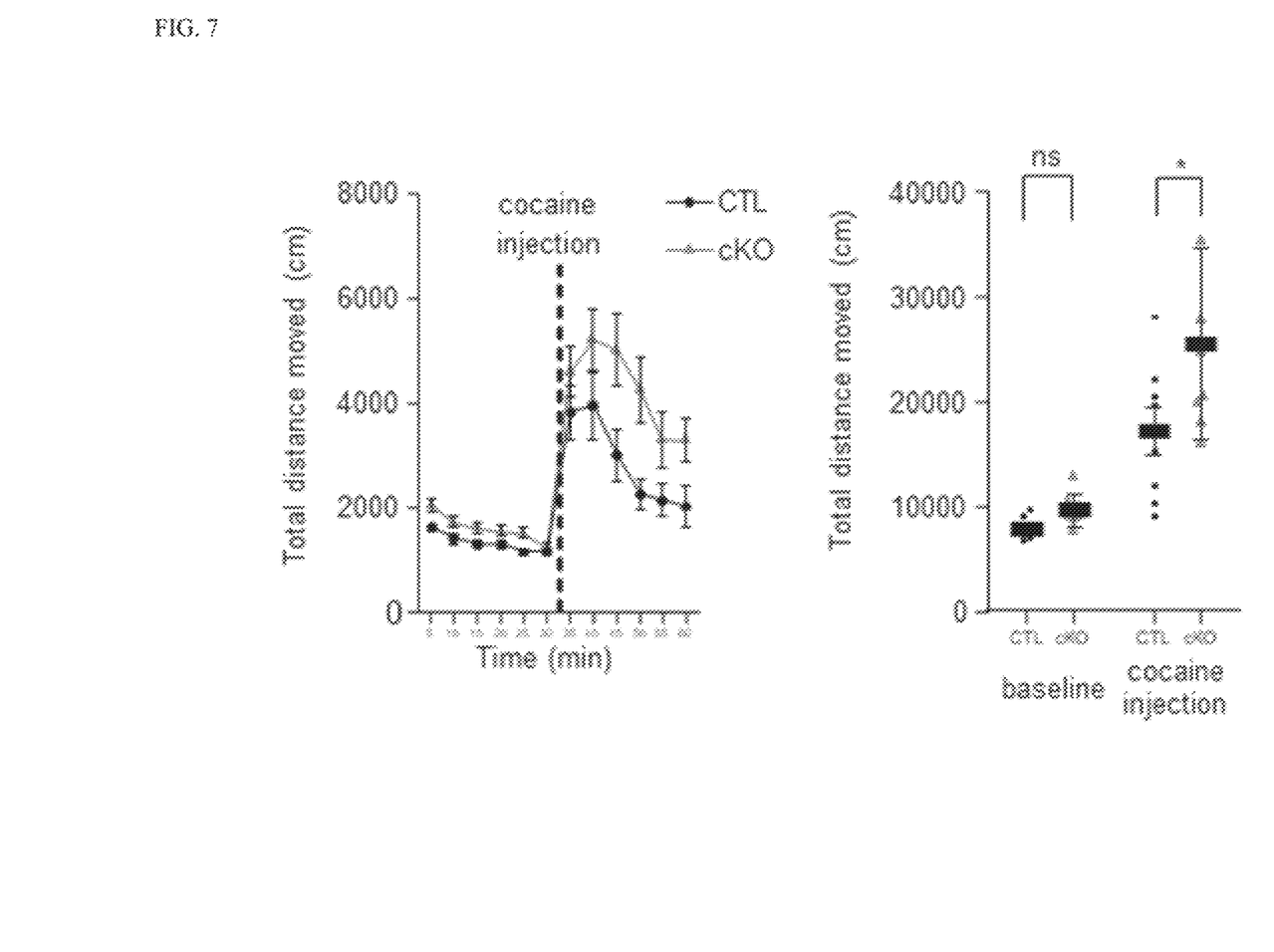
FIG. 7 shows the results of a cocaine sensitization test for a mouse prepared according to the present invention (cKO) and a normal mouse (CTL).

As a result, referring to FIG. 7, it can be seen that the mouse (cKO) in which the ANO1 gene was specifically knocked out in cholinergic neurons of the medial habenula was greatly increased in movement after the cocaine administration, compared with the normal mouse (CTL), confirming that the ANO1 gene-knocked out mouse (cKO) was sensitive to the psychoactive drug and thus showed more hyperactivity, compared with the normal mouse.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

The schizophrenia animal model according to the present invention is a novel genetic model with schizophrenia targeting a novel gene different from conventionally known DISC1, NRG1, DTNBP1, and Reelin mutant gene-introduced schizophrenia animal models. The animal model of the present invention is an ideal animal model that can replace all schizophrenia patient groups having complicated and various symptoms, and is expected to identify the correlation between genetic/environmental causes and behavior abnormalities, screen a therapeutic agent for schizophrenia, and validate the therapeutic efficacy of the agent.

The invention claimed is:

1. A genetically modified mouse in which an endogenous anoctamin 1 (ANO1) gene is specifically inactivated in cholinergic neurons,
   wherein, compared to a wild-type mouse, the genetically modified mouse shows at least one symptom selected from the group consisting of:
   (i) decreased interest in a mouse of the same kind in a 3-chamber test (3CT);
   (ii) a decrease in learning and memory of a negative stimulus;
   (iii) decreased startle response;
   (iv) a decrease in nesting behavior; and
   (v) increased movement in response to cocaine administration.

2. A method of making a genetically modified mouse in which an endogenous anoctamin 1 (AN01) gene is specifically inactivated in cholinergic neurons, the method comprising
   a) crossing a mouse whose genome comprises a nucleic acid sequence encoding Cre recombinase operably linked to a choline acetyltransferase (ChAT) promoter with a mouse whose genome comprises a pair of lox sites flanking a portion of an endogenous anoctamin 1 (ANO1) gene such that offspring are obtained; and
   b) selecting the genetically modified mouse of claim 1 from the offspring obtained in step a).

3. The method of claim 2, wherein the mouse whose genome comprises a pair of lox sites flanking a portion of an endogenous ANO1 gene has a pair of lox sites flanking exon 8 of the endogenous ANO1 gene.

4. The method of claim 2, wherein the selection of the offspring in which the ANO1 gene is specifically inactivated in cholinergic neurons is performed by immunohistochemistry.

* * * * *